United States Patent
Eugster et al.

(10) Patent No.: US 6,180,661 B1
(45) Date of Patent: Jan. 30, 2001

(54) BIOFLAVONOL-GLYCOSIDE PERESTERS AND THEIR INCORPORATION INTO PHARMACOLOGICALLY ACTIVE CONCENTRATES AND ULTRAMICROEMULSIONS

(75) Inventors: Carl Eugster, Riehen; Conrad Hans Eugster, Wallisellen, both of (CH)

(73) Assignee: Marigen, S.A., Riehen (CH)

( * ) Notice: Under 35 U.S.C. 154(b), the term of this patent shall be extended for 0 days.

(21) Appl. No.: 09/010,496

(22) Filed: Jan. 21, 1998

Related U.S. Application Data

(63) Continuation of application No. PCT/CH97/00169, filed on Apr. 28, 1997.

(51) Int. Cl.$^7$ .................................................. A01N 43/16
(52) U.S. Cl. ...................... 514/456; 424/401; 424/436; 424/451; 424/459; 424/461
(58) Field of Search .................... 514/456, 401, 514/451, 459; 424/436, 461

(56) References Cited

U.S. PATENT DOCUMENTS 5,593,691   1/1997   Eugster et al. .................. 424/461

FOREIGN PATENT DOCUMENTS

WO 98/06390   2/1998   (WO) .
WO 98/11889   3/1998   (WO) .

OTHER PUBLICATIONS

G. Zubay, *Biochemistry*, pp. xxiv–xi, 1072–1100 (1983).
Y. Yazaki, "Co–Pigmentation and the Color Change with Age in Petals *Fuchsia hybrida*", *The Botanical Magazine*, vol. 89, No. 1013, Mar. 1976, pp. 45–57.
Jeffrey B. Harborne et al., "Biochemistry of Plant Phenolics", *Recent Advances in Phytochemistry*, vol. 12 Aug. 1977, pp. 589–617.
P. Becher, "Hydrophile–Lipophile Balance: History and Recent Developments Langmuir Lecture", *J. Dispersion Science and Technology*, 1983, pp. 81–96.
J.B. Harborne, "Plant Polyhenols. VII. Chalcone and Flavonol Glycosides of Gorse Flowers", *Phytochmistry*, Sept. 1962, vol. 1 No. 3, pp. 203–207.
Daniel Perrissoud, "The Development of Cianidanol and 3–Palmitoyl–(+)–Catechin as Drugs for the Treatment of Liver Diseases", *Plant Flavonoids in Biology and Medicine*, Jul. 22–26, 1985, pp. 559–569.

Primary Examiner—James O. Wilson
(74) Attorney, Agent, or Firm—Foley & Lardner

(57) ABSTRACT

Spontaneously dispersible concentrates capable of forming ultramicroemulsions are described. The concentrates include esters of formula (I) and (II):

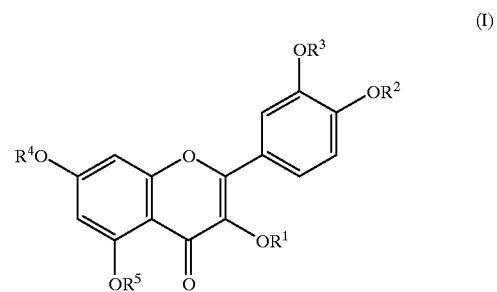

(I)

wherein (a) $R^1$, $R^3$, $R^4$, and $R^5$ each independently represents a $C_{6-22}$ alkyl, a $C_{6-22}$ alkenyl or a $C_{6-22}$ alkapolyene and $R^2$ is glucose:(1,2); (b) $R^2$, $R^3$, $R^4$, and $R^5$ each independently represents a $C_{6-22}$ alkyl, a $C_{6-22}$ alkenyl or a $C_{6-22}$ alkapolyene and $R^1$ is glucose:(1,3); (c) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rhamnose:(1,4); or (d) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rutinose:(1,5);

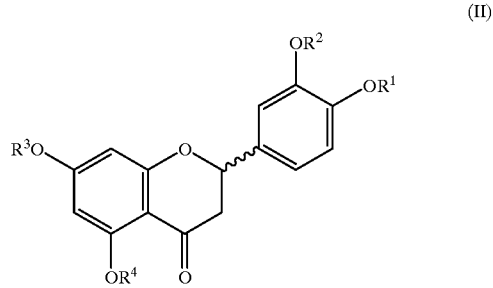

(II)

wherein
(a) $R^1$, $R^2$, and $R^4$ each independently represents a $C_{6-22}$ alkyl, a $C_{6-22}$ alkenyl or a $C_{6-22}$ alkapolyene and $R^3$ is rhamnose:(11,7); or (b) $R^2$ and $R^4$ each independently represents a $C_{6-22}$ alkyl, a $C_{6-22}$ alkenyl or a $C_{6-22}$ alkapolyene, $R^1$ is methyl, and $R^3$ is rutinose:(11,8).

9 Claims, No Drawings

BIOFLAVONOL-GLYCOSIDE PERESTERS AND THEIR INCORPORATION INTO PHARMACOLOGICALLY ACTIVE CONCENTRATES AND ULTRAMICROEMULSIONS

This application is a continuation of application Serial No. PCT/CH97/00169, filed Apr. 28, 1997.

INTRODUCTION

The PCT/CH97/00168 application of Apr. 28, 1997 (EPA 97'917'205-3) describes ultramicroemulsions from spontaneously dispersible concentrates comprising esters with bioflavonoid compounds having antitumor, antiviral, virucidal and/or antiparasitic efficacy. Thanks to the demonstrated solubilization of the active principles, in the form of thermostable, oil-in-water emulsions possessing very small micelles in the lowest nanosize region, an excellent bioavailability can be achieved for them. In the course of an intensive elaboration of the properties of this class of compounds, it was found that surprisingly also the glycoside peresters of the studied bioflavonoids have comparative pharmacological properties, provided that they are also formulated correspondingly. In such manner they can be used for curative as well as preventive purposes. Because they are non-toxic and yet highly active, members of this group of natural agents, which up-to-now is only scarcely investigated, these findings can be instrumental in opening a broad therapeutic window. The application of the fatty-tail principle for the esterification and the incorporation of the newly obtained glycoside esters into inventive, spontaneously dispersible concentrates form a systematic two step-approach—the extension of a procedure which has already been described in principle in the Swiss patent CH 683'426 (U.S. Pat. No. 5,593,691) and in the CH patent application 2239-95 (PCT/CH96/00280; EPA 96'925'634-6). The subject of the present invention consequently are Flavonol-glycoside peresters as characterized hereafter, their incorporation into pharmaceutically practicable application forms, as well as their use as medicaments having efficacy against tumors, eczemae, psoriasis, viral and parasitic infections and metabolic disorders.

DESCRIPTION OF THE INVENTION

1.0 Definition of Scope

Flavonol-Glycoside-Peresters, as the term is used in this invention, comprise the following compounds:

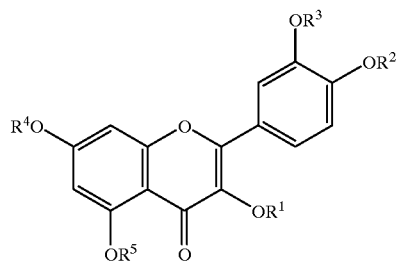

(I)

1. QUERCETIN ($R^1$–$R^5$=H); Merck-Index 11.8044
2. SPIRAEOSIDE ($R^1$, $R^3$–$R^5$=H; R=Glucose) $4'$-β-D-Glucopyranosidoquercetin
3. ISOQUERCETIN ($R^2$–$R^5$=H; R=hu 1=1 =Glucose) 3-β-D-Glucopyranosidoquercetin
4. QUERCITRIN ($R^2$–$R^5$=H; R=hu 1=1 =Rhamnose); Merck-index 11.8047 3-α-L-Rhamnopyranosidoquercetin; Merck-index 11.8044
5. RUTIN ($R^2$–$R^5$=H; R=hu 1=1 =Rutinose); Merck-index 11.8276/77 3-[α-L-Rhamnopyranosil (1→6)-β-glucopyranosil]-quercetin=3-α-L-Rutinosylquercetin

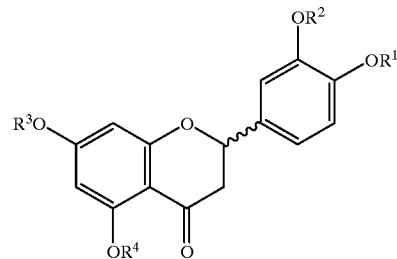

(II)

6. ERIODICTYOL ($R^1$–$R^4$=H); Merck-index 11.3616
7. ERIODICTIN ($R^1$, $R^2$, $R^4$=H; R=hu 3=1 =Rhamnose) 7-α-L-Rhamnopyranosido-eriodictyol
8. HESPERIDIN ($R^2$, $R^4$=H; ($R^1$=$CH_3$; $R^3$=Rutinose) 7-β-Rutinosyl-4'-methyl-eriodictyol; Merck-Index 11.4591 whereby all R=H stand for a saturated or unsaturated carbonic acid of the type $C_{6-22}$ alkyl, $C_{6-22}$ alkenyl or $C_{6-22}$ alkapolyene.

1.1 Foundations

A selected number of derivatives of QUERCETIN, produced according to formula (I),1 with the glycosides 2, 3, 4, 5, and of its biogenetic precursor ERIODICTYOL (II),6 produced with the glycosides 7 and 8, was made the subject of the present investigation. It can firstly be said that these compounds widely occur in dicotyledones (see the tables 8.15 and 11.1 in "The Flavonoids", Ed. J. B. Harborne, T. J. Mabry, H. Mabry, Academic Press, New York 1975) and are, in part at least, easily accessible. A second reason is that many of them have quite thoroughly been studied also in medicine (cf. V. Cody, E. Middleton, J. B. Harborne: "Plant Flavonoids in Biology and Medicine", A. R. Liss, New York, 1986). Note in particular, that the compounds 4, 7 and 8 are components of the once intensely investigated substance "Vitamin P" (the permeability vitamin); see H. Vogel: "Chemie und Technik der Vitamine", Enke, Stuttgart, 1940. See also H. Wagner in "Recent Advances in Phytochemistry", Vol. 12, p. 589; Ed. T. Swain, J. B. Harborne, C. F. VanSumere; Plenum Press, New York, 1979. Cf. further Jirina Spilková and Josef Hubik: Biologische Wirkungen von Flavonoiden. Pharmazie in unserer Zeit, January 1988, pp.1–9; Apr. 1992, pp. 174–182.

1.2 Significance of the Appropriate Solubilization of the Active Principles

In CASE CH-2088/95; PCT/CH97/00168 of Apr. 28, 1997 it was demonstrated for selected bioflavonoid esters that the application of the fatty-tail principle to the formation of derivatives leads to important physicochemical changes in their properties, and particularly to a strongly enhanced lipophilic character, coupled with a noteable depression of the melting point (if compared with the starting material). These properties facilitate emulsification and render aqueous ultramicroemulsions of very good stability. As a consequence, the targeted delivery (i.e. the bioavailability) and hence also the bioreactivity of the inventive agents are also decisively potentiated.

1.3 Production of the Peresters

The new procedure is being applied with naturally occurring Flavonolglycosides, which can be found in many plants. The glycoside perester compounds corresponding to the formulae (III) and (IV):

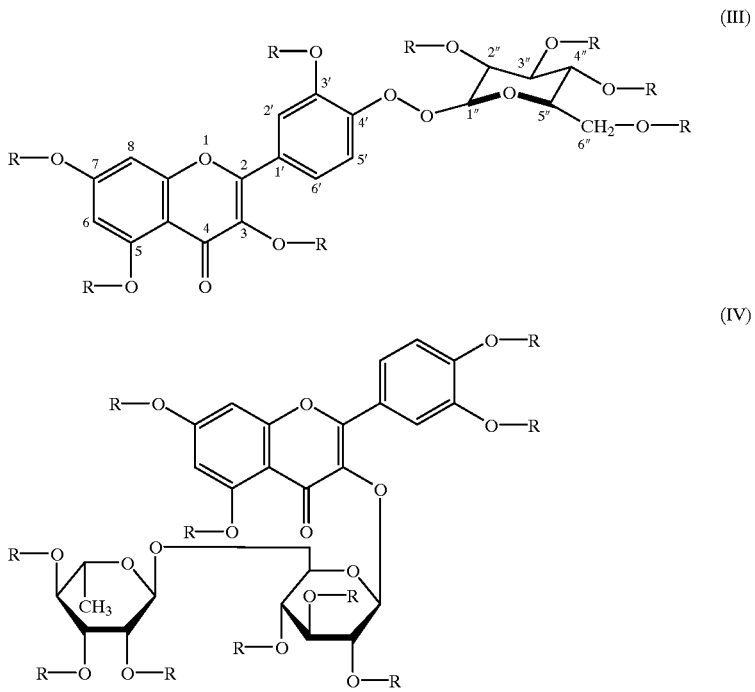

(III)

(IV)

can be prepared in accordance with the following procedures:

1.31 Fatty Acid Esters of Spiraeoside, Conforming to Formula (I), 2

Spiraeoside is a flavonolglycoside, which occurs with ca. 1.2% in the dried leaves of the flowers of *Spiraea ulmaria* L., sive *Filipendula ulmaria* (L.) Maxim. It was discovered by E. Steinegger and P. Casparis [Pharm. Acta Helv. 1945, 20, 154, 174]; later investigations revealed its existence in many plants, particularly in species, which since ancient times were known and used in popular medicine, such as, e.g., in a proportion of 1% in onion peels (*Allium cepa* L.) [K. Hermann, Naturwiss. 1956, 43, 158; Arch. Pharm. 1958, 291, 238]; of 3% in dried flowers of *Hamamelis japonica* S. & Z. [L. Hörhammer and R. Griesinger, Naturwiss. 1959, 46, 427], in the seeds of horse-chestnuts *Aesculus hippocastanum* L. [J. Wagner, Naturwiss. 1960, 47, 158], in the leaves of diverse kinds of hamamelidaceae [K. Egger and H. Reznik, Planta, 1961, 57, 239] and in the flowers of gorse (*Ulex europaeus* L. [J. B. Harborne, Phytochem. 1962, 1, 203].

Newer publications mention the presence in flowers of gardening hybrids of Fuchsia [Y. Yasaki, Botanical Magazine (Tokyo) 1976, 89, 45], as well as in numerous hybrids of gardening roses [K. Nayeshiro and C. H. Eugster, Helv. Chim.Acta 1989, 72, 985]. In the last named cases, spiraeoside contributes decisively to the stabilization of the anthocyanine complexes, which are responsible for colouring.

Despite the general presence of spiraeoside in medicinal plants, the compound has rarely been studied scientifically for its role in traditional popular healing, and no effort was made so far to investigate the pharmaceutical properties of the pure substance.

The chemical structure of spiraeoside as 4'-β-D-Glucopyranosylquercetin was determined by E. Steinegger et al. (loc.c.) and by L. Hörhammer and R. Hänsel, Arch.Pharm. 1954, 287, 36, with the help of classical methods. The analytical control, employing modern equipment and methods, was carried out in connection with the purity assay for the freshly isolated starting material which was then esterified as described in the present invention. It confirmed the chemical structure as given in formula (V):

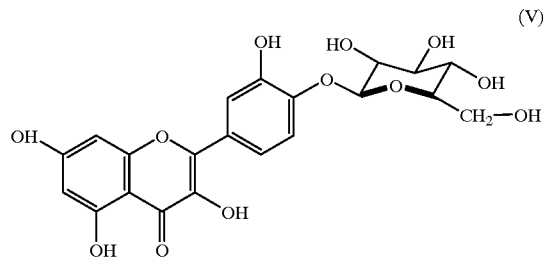

(V)

Sufficient quantities of (V) can be obtained from the indicated sources by relatively simple extraction and enrichment steps. In the present case, the commercially available drug 'Flos Spiraeae ulmariae' was processed. Following processes of mild extraction, separation, column chromatography and cristallisation, compound (V) was isolated and subsequently esterified using a fatty acid chloride, in order to obtain compound (VI). Of importance is the enhanced stability of the ester function at C(5), as compared to that of Quercetin esters.

Isolation of Spiraeoside (V)

500 g of 'Flos Spiraeae' (Dixa St.Gallen, berries) are kept standing in the percolator with 4 L of methanol-water 4:1 during 2 days. The produced, yellowish-brown percolate is evacuated to ca. 250 ml and extracted 4 times in the separatory funnel with 250 ml each time of n-butanol. The pooled butanol solutions are then evacuated at 5 Torr, and the oily residue is taken up in 250 ml of acetic acid-water-methanol-ethylacetate 6:34:20:10 and chromatographically purified with a column of 0.8 kg polyamide powder (Macherey-Nagel, SC6) or optionally with water-pyridine 97.5:2.5 on Sephadex G-10 (Pharmacia). The resulting, spiraeoside-containing fractions are pooled and evaporated i.v.; the residue is crystallized in little hot 15%-acetic acid. Very pure spiraeoside can be obtained by repeated chromatography over cellulose powder (Avicel®, Merck, art. 2331) using 13%-acetic acid. The product has clear yellow needles, mp. (vac., uncorr.) 211.5–212.5° C.

Production and characterization of Octalauroylspiraeoside

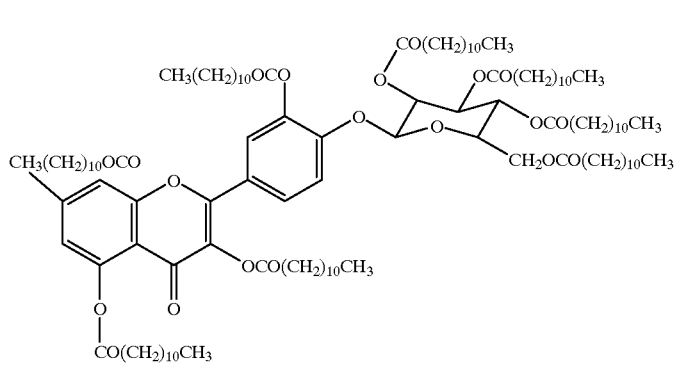

(VI)

In a small three-neck flask, with $N_2$-inlet, magnetic stir bar, drop funnel and cooler, one dissolves 214 mg of spiraeoside in 2 ml of waterfree pyridine by warming up lightly, then diluting the solution with 5 ml of 1,2-dichloroethane and 10 mg of 4-dimethylaminopyridine. Subsequently cool down under $N_2$ to 0° C., slowly add dropwise, under good stirring, a solution of 0.87 ml of lauroylchloride in 5 ml of 1,2-dichlorethane. Then let the temperature rise to RT and stand for 12 h. The clear, almost colourless solution is then diluted with $Et_2O$ and the produced suspension washed 5 times in the separatory funnel with strongly diluted $H_2SO_4$ and at the end with brine. Treating the solution with diluted hydrogencarbonate solution may lead to considerable emulsification, if the batch contains excessive lauroyl chloride. In order to avoid foaming in a simple way, slowly filter the dried solution using a short column with calcium carbonate, eluent: $Et_2O$ or a mixture of dichloromethane/ethyl acetate. After drying over $Na_2SO_4$ and processing as usual, one obtains a pale yellowish, vesicular foam, yield 0.94 g. It can be crystallized from $CH_2Cl_2/CH_3CN$ or from 2-propanol: weakly yellowish crystals are formed, mp. 82.5–85° C.

$[\alpha]_D$: −11.7° (c=1.034; $CHCl_3$).

UV: ($CH_2Cl_2$): 232 (26'900), 254 (20'400), 311 (26'100)

IR: ($CH_2Cl_2$): 3048w, 2932ss, 2853s, 1762s, 1651m, 1622m, 1510m.

$^1$H-NMR: ($CDCl_3$, 300 MHz): 0.8–2.7 (proton signals of the ester component); 3.8 to 5.8 (signals of the protons on the sugar part); 6.76 (d, J=2.4, H-C(5)). 7.02 {d, J=8.8, H-C(5')}; 7.22 {d, J=2.4, H-C(8)}; 7.44 {d, J=2.2, H-C(2')}; 7.59 (dd, J=8.8 and 2.2, H-C(5')); The original OH-protons at 8.59/9.50/10.79 and 12.41 ppm have disappeared.

$^{13}$C-NMR: ($CDCl_3$, 75 MHz): i.a. 9 carbonyl signals at 173.1/172.6/171.9 (three-fold intensity)/171.1/170.7/170.4/169.9 ppm.

Elemental analysis (incineration):

$C_{117}H_{196}O_{20}$ (1922,74) Calc. C 73,08 H 10,28% Found C 72,89 H 10,91%

In a comparative manner, also the peresters formed with capronic acid, undec-10-enoic acid, palmitic acid and stearic acid chlorides can be produced.

1.32 Fatty acid esters of Vitamin P (Quercetin-3-rutinoside) Production of Rutindecalaurate

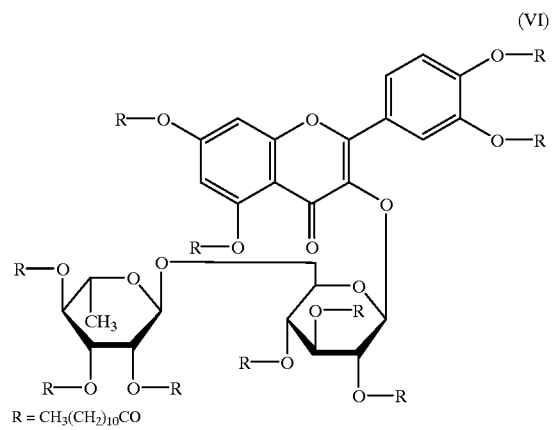

(VI)

$R = CH_3(CH_2)_{10}CO$

Commercial Rutintrihydrate in accordance with formula (VI), in which R=H:

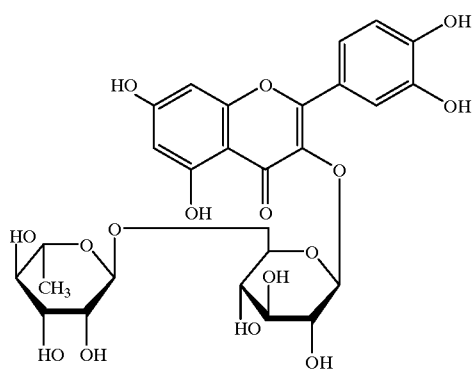

was dried during 20 h at 100° C./0.01 Torr. 0.92 g of waterfree Rutin were then dissolved in 5 ml of abs. pyridine and 5 ml of abs. dimethylformamide by warming up and diluting subsequently with 10 ml of 1,2-dichloroethane. After cooling down under $N_2$ and stirring, add dropwise 3.59 ml of lauroylchloride in 10 ml of 1,2-dichloroethane. Subsequently let the batch slowly rise to RT and then stand it for 20 h, with constant stirring. Add a sufficient amount of ether, so that the washing operation with strongly diluted $H_2SO_4$ and water renders a clearly separated upper phase. After drying over $Na_2SO_4$ and customary processing, including drying the residue in high vacuum, one obtains a honey-like clear brownish oil. Yield ca. 90%. Analytical data:

UV: (hexane, qualitatively): $\lambda_{max}$ 202 nm, 250, sh 293, sh 306

$[\alpha]_D$:=−28.5° (c=0.82 in chloroform)

IR: (dichloroethane): no bands in the OH-range; 3045w, 2625ss, 2855s, 1750s, 1646m, 1629m, 1504w.

2.0 Production of Spontaneously Dispersible Concentrates and of Aqueous Ultramicroemulsions Because of their pronounced lipophilic properties, the described compounds according to the formulae (I) to (VI) are insoluble in water. In order to enable them to penetrate the membrane barrier of tumor or host cells and of the protein hull of viruses or parasites and then to spread in the cell plasma and inside the virus/parasite, these compounds must first be solubilized in appropriate manner in the aqueous medium. This is achieved over 2 steps: first the production of spontaneously dispersible concentrates, which comprise the active principles as an integrative, micellar component of the system, and second the addition of distilled water, 5%-glucose solution or physiological sodium salt solution (Ringer solution) in a proportion 1:20 to 1:1'000'000.

By preparing thermodynamically stable oil-in-water ultramicroemulsions, employing selected cotensides (i.e. hydrotropic agents) on the one hand, and appropriate tensides (surfactants) on the other hand, it becomes possible to achieve an optimal degree of solubilization of these ester compounds and of their biolociical delivery and hence a high bioavailability and bioreactivity at or in the target cell.

All experimental observations gained with stable ultramicroemulsions of this kind can be uniformly interpreted by means of the concept that the inventive solubilization system produces in the aqueous phase organized aggregates, which are MICELLES. These micelles possess a more or less globular shape, having a hydrodynamic radius of less than 10 nm. They are thermodynamically stable. The tensides and cotensides are capable at the phase-boundary of the microemulsion of hindering SELF-DIFFUSION. This means that no mixing takes place between the outer aqueous phase of the microemulsion and its inner, oily phase, which contains the ester compounds according to the formulae (I) to (VI), solubilized in the coemulgator, i.e. the biotenside solvent employed as an essential component of the spontaneously dispersible concentrate. In the inner, oily phase, the molecules of the selected esters are thus present in monomeric or in oligomeric form. The micelles, which comprise in their micellar core the solubilized active substances, are coated by a tenside layer or bilayer and are thus rendered elastic. This enables them to penetrate through the plasma membrane of the tumor cell or the virus- or parasite-infected host cell, and also through the envelope of the virus. This diffusion process takes place on account of thermal molecular movements exclusively. In biological systems they are not related to metabolic energy. The fractal dimensions of these membranes allow the build-up of considerable gradients, i.e of differentials in concentration. The velocity of the ensuing diffusion process and the volume of transport through the membrane of the target cells are a function of:

1. the concentration difference in the two compartments outside and inside the cell
2. the radius of the particles (i.e. the micelles) enclosing the diffusing active substance
3. the viscosity of the diffusing aqueous solution (emulsion)
4. the temperature.

The proper solubilization of the active substances, which are practically insoluble in water, by means of surfactants (coemulgator plus tensides) is a conditio sine qua non for achieving self-diffusion and hence active transport of the biologically effective substances across the membranes of living cells. As can be seen from the table, one globular "micelle" having a hydrodynamic radius of one centimeter possesses a volume of 4.189 $cm^3$ and a phase surface of 12.564 $cm^2$. In contradistinction: a number of $10^{18}$ micelles having each a hydrodynamic radius of $10^{-6}$ cm(=10 nm) only, together possess the same volume of 4.189 $cm^3$ and yet cover up a total phase surface of 1'256.4 $m^2$.

| MICELLES: PROPORTION between VOLUME and SURFACE AREA ||||
|---|---|---|---|
| NUMBER of the MICELLES | Hydrodynamic RADIUS of the micelles | VOLUME Of the micelles | TOTAL SURFACE AREA of the micelles |
| 1 | 1 cm | 4.189 $cm^3$ | 12.564 $cm^2$ |
| $10^3$ | 0.1 cm = 1 mm | " | 125.64 $cm^2$ |
| $10^6$ | 0.01 cm | " | 1'256.4 $cm^2$ |
| $10^9$ | 0.001 cm | " | 12'564 $cm^2$ |
| $10^{12}$ | 0.0001 cm = 1 μm = 1'000 nm | " | 125'640 $cm^2$ |
| $10^{15}$ | 0.00001 cm = 100 nm | " | 1'256'400 $cm^2$ |
| $10^{18}$ | 10 nm | " | 1'256.4 $m^2$ |
| $10^{21}$ | 1 nm | " | 12'564 $m^2$ |

Spheric volume=4/3 $\pi r^3$

Spheric surface=4 $\pi r^2$

Conclusion

Due to the enormous total surface area, which is taken up in the inventive ultramicroemulsions by the micelles having a hydrodynamic radius of 2.2 to 3.0 nm, in addition to the increased diffusion capability, also the Theological distribution (the "spreading") is significantly enhanced. Hence, the bioavailability, as well as the bioreactivity of the antitumor agents carried in the core of the micelles (and maintained there in monomeric or oligmeric solution), are also notably improved. This will allow a considerable reduction of the critical dosage required. This, in turn, causes a reduction or complete elimination of unwanted, disturbing side-effects.

The "packing density" achieved with the spontaneously dispersible, stable MARIGENOL®-concentrates obeys the exponential relationship illustrated above: the smaller the particle size of the micelles, the greater the packing density obtainable. Of decisive importance is the correct formation of the inner phase, its balanced proportion with respect to the entire concentrate and the choice of the suitable tensides.

2.1 The inventive spontaneously dispersible concentrates comprise:

0.1 to 5% by weight of one of the esters according to the formulae (I) or (II), or of a combination of such esters, and 0.1 to 5% by weight of a known pharmaceutical, dermatological and/or cosmetic active substance, 5 to 25% by weight of a hydrotropic agent, which is the pharmaceutically acceptable coemulgator or solvent, 0 to 5% by weight of a Good-buffer or of 3-[(3-Cholamidopropyl)-dimethylammonio]-propansulfonate (CHAPS) and/or DMSO (Dimethylsulfoxyde), up to 90% by weight of a pharmaceutically acceptable surfactant or surfactant mixture, and optionally up to 10% by weight of a vitamin or provitamin, up to 10% by weight of a penetration enhancer, radical scavenger and/or stabilizer.

The inventive aqueous ultramicroemulsions comprise:

0.1 to 5% by weight of a spontaneously dispersible concentrate as defined above, 85 to 99.9% by weight of distilled water, physiological sodium salt solution (Ringer solution) or 5% glucose solution, up to 10% by weight of carriers, customary excipients and/or diluents.

These aqueous ultramicroemulsions are characterized by the following properties: a reduced surface tension of 28–32 mNm$^{-1}$, a low inner viscosity (showing a dynamic viscosity η at 20° C. around 1.0 cP=10$^{-3}$ Pa.s), a very small and homogenous particle size and a good thermodynamic stability (no coalescence, no agglomeration of the micelles, no autocondensation of the tensides; that is to say that no "self assembly" is occurring as due to the chemical degradation of the tensides). The active principles are found in monomeric or oligomeric solution, packed in the micellar core. Due to the balanced proportions, even with very high degrees of dilution, the tenside coated umbrella of the micelles is preserved. This also prevents so-called "instability or Marangoni effects". Thanks to these properties, the inventive ultramicroemulsions permit high capillary diffusion. Their penetration potential at the cell membrane of defective or abnormal cells is excellent and is followed by very good spreading (rheological distribution) inside the cell. The consequence is that the described solubilization system makes for a high bioavailability and hence also bioreactivity of the active principles which are carried in it, coupled with a reduced or no toxicity at all.

The surfactants or surfactant mixtures to be employed according to the invention can be anionic, cationic, amphoteric or non-ionic. Ideally, they are non-ionic and have an HLB-value (i.e. a hydrophilic-lipophilic balance) of between 2 and 18; preferably, it is between 2 and 6 on the one hand and 10 and 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both so-called water-soluble soaps and water-soluble synthetic compounds. Suitable soaps are the alkali metal salts, alkaline earth metal salts or optionally substituted ammonium salts of higher fatty acids ($C_{12-22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids. However, more frequently used surfactants are so-called synthetic surfactants, in particular fatty sulfonates, fatty sulfates, sulfonated benzimidazole derivatives or alkylaryl-sulfonates. The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaphthalene-sulfonic acid or of a naphthalenesulfonic acid/formaldehyde condensation product. The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy-adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit. The following may be mentioned as examples of non-ionic surfactants: nonylphenol polyethoxyethanols, castor oil polyglycol ethers, polypropylene/polyethylene oxide adducts, tributylphenoxy-polyethoxy-ethanol, polyethylene glycol and octylphenoxy-polyethoxyethanol. Moreover, fatty acid esters of polyoxyethylene-sorbitan, such as polyoxyethylene sorbitan trioleate, are also suitable. The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi-(2-chloro-ethyl)-ethyl-ammonium bromide.

When preparing the inventive spontaneously dispersible concentrates, special preference is given on the one hand to phosphoric acid ester tensides, such as:

Tristyrylphenolpolyoxyethylene-18-phosphoric-acid-ester-triethylamine, (TEA)-salt tenside, with formula:

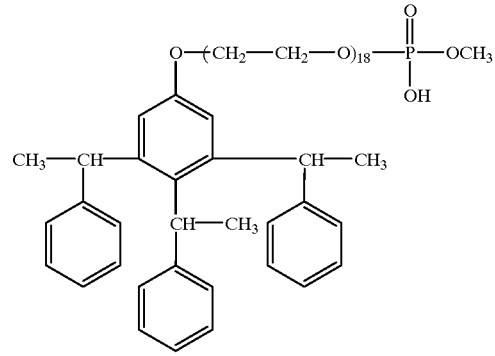

Soprophor FL (RHÔNE-POULENC)

Nonylphenol-10-polyoxyethylene-mono/dimethylphosphoric-acid-ester [Diphasol® 3873, (CIBA-GEIGY); or the identical Sermul® EA 188 (SERVO)]:

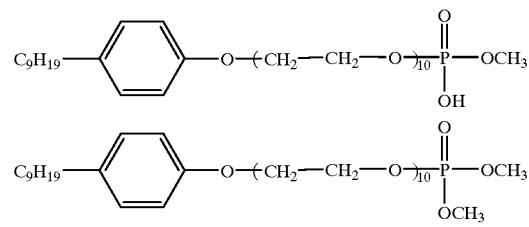

Diphasol® 3873 (CIBA-GEIGY)

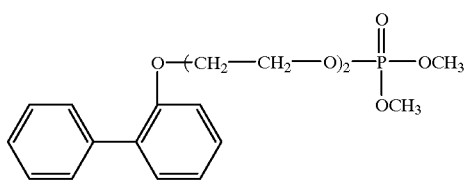

Tenside 508, (CIBA-GEIGY);
Tinovetin® JU (CIBA-GEIGY), a hydroxybiphenyl-10-ethoxy-phosphoric acid ester
Butyl-mono-4-ethoxy-phosphoric acid ester (Zerostat® AT, CIBA-GEIGY), and

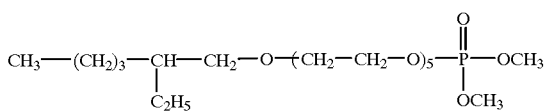

Zerostat® AN (CIBA-GEIGY), respectively
and on the other hand to betain compounds, i.e. amphoteric, salt- and water-free imidazole derivatives, having an isoelectric/isoionic point near 7, such as, e.g., the compound:

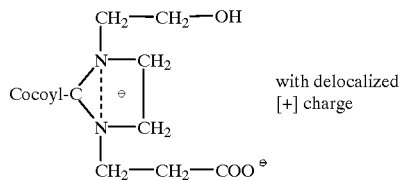

Amphonyl CA-AA (CHEMAG).

Furthermore, so-called "multi-functional glucose derivatives", such as, e.g., Glucate® SS (Methylglucose-sesquistearate) and Glucamate® SSE-20 (PEG-20-methylglucose-sesquistearate) of Amerchol, Edison, N.J., are also being used. In certain cases, good results can also be achieved when non-ionic surfactants of the "TWEEN®"-class are used (Atlas Chem. Ind. Inc. or ICI Speciality Chemicals), so-called polyoxyethylene-sorbiton-monoesters or "Polysorbate" 20-85 in the CTFA classification.

The following compounds may be employed as the pharmaceutically acceptable solvent which acts as the hydrotropic agent (i.e. the coemulsifier), for example: esters of an aliphatic alcohol ($C_{3-18}$) with an aliphatic carboxylic acid ($C_{10-22}$), such as isopropyl laurate, hexyl laurate, decyl laurate, isopropyl myristate and lauryl myristate; hydrocarbons having a straight carbon chain ($C_{12-32}$) which is substituted by 6 to 16 methyl groups and which can have up to 6 double bonds, examples which may be mentioned being terpenes, such as polymethylbutanes and polymethylbutenes. Monoesters of ethylene glycol or propylene glycol with an aliphatic carboxylic acid ($C_{6-22}$), such as propylene glycol monolaurate and propylene glycol monomyristate. Esters of an aliphatic alcohol ($C_{12-22}$) with lactic acid, such as, for example, myristyl lactate or, preferably, lauryl lactate. Monoesters or diesters of glycerol with an aliphatic carboxylic acid ($C_{6-22}$), such as, for example, glyceryl caprylate or Miglyol® 812 neutral oil (Oleum neutrale). Esters of a poly(2-7)ethylene glycol glycerolether having at least one free hydroxyl group with an aliphatic carboxylic acid ($C_{6-22}$), such as, for example, aliphatic alcohols ($C_{12-22}$), thus, inter alia, dodecanol, tetradodecanol, oleyl alcohol, 2-hexyldecanol and 2-octyldecanol. Esters containing at least one free hydroxyl group, of poly-(2-10)glycol with an aliphatic carboxylic acid ($C_{6-22}$), monoethers of a polyethylene glycol with an aliphatic alcohol ($C_{12-18}$), such as, for example, polyoxyethylene-(C10) octylether. Heterocyclic compounds such as 1-methyl-2-pyrrolidon. Biotenside terpinyl esters according to the general formula (VII):

$$R^3—COO—R^4 \qquad (VII)$$

in which $R^3$ is a $C_{6-31}$alkyl or a $C_{9-31}$alkenyl/alkapolyene group and $R^4$ is citronellyl-, farnesyl-, geranyl-, isophytyl- or phytyl-.

Before their application into spontaneously dispersible concentrates all technical tensides have been cleaned by filtration or by chromatography over aluminum-oxide with an inert solvent as eluent, such as tetrahydrofurane, ethyl alcohol or dichlormethane.

2.2 COMPOSITION EXAMPLES for inventive, spontaenously dispersible concentrates, which comprise active principles according to formulae (I) to (II) and which, if diluted with distilled water or 5%-glucose solution or physiological sodium salt solution (Ringer solution), form thermodynamically stable ULTRAMICROEMULSIONS, having micelles of a hydrodynamic radius of 2.2 to 3.0 nm.

a) 0.1 to 5% by weight of one or several active principles in accordance with formulae (I) or (II),
   0 to 5% by weight of a known, synergistically active pharmaceutical, dermatological and/or cosmetic substance,
   5 to 25% by weight of isopropyl myristate, isopropyl palmitate or of neutral oil, such as Miglyol® 812 (Dynamit Nobel or Hüls),
   0 to 5% by weight of a Good-buffer or of 3-[(3-Cholamido-propyl)-dimethylammonio]-propansulfonate (CHAPS) and/or DMSO (Dimethylsulfoxyde),
   0 to 45% by weight of a phosphoric acid ester surfactant, as e.g. Diphasol® 3873 (CIBA-GEIGY), Tenside 508 (CIBA-GEIGY), Zerostat® AN or AT (CIBA-GEIGY), Tinovetin® JU (CIBA-GEIGY), Soprophor® FL (RHÔNE-POULENC),
   5 to 90% of Invadin JFC 800% (CIBA-GEIGY), and/or TWEEN® 20-85 (ICI Surfactants), a polyoxyethylene-(20)-sorbitan ester tenside, and optionally
   up to 10% by weight of a vitamin or provitamin,
   up to 10% by weight of a stabilizer, penetration enhancer, excipient, diluent, or a combination thereof.

b) 0.1 to 2% by weight of one or several active principles in accordance with formulae (I) to (II),
   5 to 25% by weight of one or several biotenside terpinyl esters conforming to the general formula (VII)

$$R^3—COO—R^4 \qquad (VII)$$

in which $R^3$ is a $C_{6-31}$alkyl or a $C_{9-31}$alkenyl/alkapolyene group and $R^4$ is citronellyl-, farnesyl-, geranyl-, isophytyl- or phytyl-,
   30 to 45% by weight of Invadin® JFC 800% and/or of a Tween® surfactant and/or Amphonyl® CA-AA,
   the rest up to 100% by weight of Soprophor® FL or Diphasol® 3873.

c) 1% by weight of an agent according to formulae (I) or (II),
   4 to 9% by weight of 2-pentanol or glycerol waterfree or DMSO 15 to 20% by weight of citronellyl-10-undecenoate ($C_{11:1}$-(±)-β-Citronellyl ester) or of citronellyl-laurate ($C_{12:0}$-(±)-β-Citronellyl ester), 30% by weight of Invadin® JFC 800% and/or TWEEN®-20, the rest up to 100% by weight of Soprophor® FL and/or Diphasol 3873.

N.B.: INVADIN® JFC 800% (CIBA-GEIGY) is a water-free tert. octylphenyl-polyoxyethylene ether tenside, having 9 to 10 oxyethylene groups. TWEEN®-surfactants No. 20-85 (ICI Speciality Chemicals) are non-ionic polyoxyethylene sorbitan ester tensides, CTFA classification: Polysorbate 20-85.

Example for the pharmaceutical production of a system's preparation containing the inventive concentrates in the form of "multiple units".

| a) Granulation (granules and pellets) | |
|---|---|
| Metolose ® 90 SH-4000 (Shin-Etsu Chemical) | 90.0 g |
| Avicel ® PH-101 | 80.3 g |
| Inventive, spontaneously dispersible concentrate | 139.4 g |
| Aerosil ® 200 | 80.3 g |
| Σ | 390.0 g |

Granulation in the high speed mixer or the fluidized bed, with the addition of 110 g ethanol, sieving on a 18 to 42 mesh screen with crushing, drying for 24 h at 40° C.

b) Enteric and sustained release coating: prepared in the fluidized bed with AQOAT® AS-HG (Shin-Etsu Chemical) and talc.

c) Composition of finished granules or micropellets

| | |
|---|---|
| Core Material | 44% by weight |
| Inventive concentrate | 25% by weight |
| Enteric coating | 31% by weight |
| Σ | 100% by weight |

N.B. The pellets or granules according to a) can also be filled without prior coating into capsules which are made of AQOAT® (HPMC-AS-M or HPMC-AS-N), have been sealed with acetone/ethanol 1:1 and can thus perform the functions of pH-control and slow release.

3.0 Biological Assays

The antitumour/antiviral/antiparasitic activity of the spontaneously dispersible concentrates comprising active substances prepared according to the composition examples a) to c) given in 2.2 above, is confirmed by the following test results:

3.1 In-Vitro Assays Using Suitable Tumour Cell Lines

A biological assay system using microtiter plates and serial dilutions has been developed. Batches of $10^4$ tumour cells per ml were set up in culture medium RPMI 1640 and inactivated with 10% of fetal calf serum (GIBCO); they are spread at a density low enough to enable them to grow during the assay, in so-called non-confluent monolayers. Samples are added after 6 to 24 h, with 100 μl per row, to which 100 μl of medium are added in the first well. Half of this mixture is withdrawn, transferred into the next well and again treated with 100 μl of medium, etc. This results in an n½ geometrical serial dilution.

In the plaque assay, the samples are incubated at 37° C. for 3 to 5 days under 3½% of $CO_2$. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

3.2 Testing Cell Toxicity 3.21 Cell tocicity of the MARIGENOL®-CONCENTRATES tested with Py6-Cells (Polyoma virus transformed 3T3 mouse-fibroblasts)

Py6 cytotoxicity-test

Apr. 24–28, 1995

| 1%-concentrate | 24 h Exposure Concentrate A.S. | 48 h Exposure Concentrate A.S. | 72 h Exposure Concentrate A.S. |
|---|---|---|---|
| OCTALAUROYL-SPIRAEOSIDE (with CHAPS | 32'000 3.2 Mio. | 64'000 6.4 Mio. | 128'000 12.8 Mio. |
| OCTALAUROYL-SPIRAEOSIDE (with Tween-20) | 16'000 1.6 Mio. | 64'000 6.4 Mio. | 128'000 12.8 Mio. |

Greatest cytotoxic dilution:

calculated on the concentrate and active substance-content

N.B.: On the subject of the eternalized Py6cells cf.: "Biochemistry", Coordinating Editor Geoffrey L. Zubay, Addison-Wesley Publishing Company, 1983, p.1079.

See also "Molecular Cell Biology", second Edition, by J. Darnell, H. Lodish, D. Baltimore; Scientific American Books, Chapter 5: Viruses, Structure and Functions, pp. 177–188. New York, 1990 (W.H. Freeman & Co.)

3.22 Cell tocicity of the MARIGENOL®-CONCENTRATES (continued)

Py6 cytotoxicity-test

Mar. 28–Apr. 2, 1996

| 1%-Concentrates | 48 h Exposure Concentrate A.S. | 72 h Exposure Concentrate A.S. | 72 h Greatest still cytotoxic Dilution A.S.-Concentration in μMol |
|---|---|---|---|
| QUERCETIN-PENTALAURATE | 40'000 4 Mio. | 80'000 8 Mio. | 0.103 |
| OCTALAUROYL-SPIRAEOSIDE | 160'000 16 Mio. | 320'000 16 Mio. | 0.016 |
| RUTINDECA-LAURATE | 160'000 16 Mio. | 160'000 16 Mio. | 0.014 |

Greatest cytotoxic dilution:

calculated on the concentrate and active substance-content; Final test concentration indicated in μMol.

N.B. Composition of 1%-concentrates:

1% by weight of active principle

12% by weight of $C_{11:1}$-(±)-β-CITRONELLYL-ESTER

87% by weight of Invadin JFC 800%/Soprophor FL 1:1

4.0 Antiparasitic Tests

SWISS TROPICAL INSTITUTE, BASEL

In-vitro assays, WHO-screening as SOP

| Parasite | Strain | Stage | Standard | Test N° |
|---|---|---|---|---|
| T.b.rhodesinense | STIB 900 | trypomastigotes | Melarsoprol | T9611 |
| L.donovani | MHOM-ET-67/L82 | amastigotes | Pentostam | L9604/05 |
| T.cruzi | MHOM/Br/00/Y | trypomastigotes | Benznidazol | C0606/08 |

The assays were conducted at the Swiss Tropical Institute, Basel (Prof.Dr. Ronald Kaminsky and Mrs. Yvonne Grether). The aim was to find out whether there was selective activity in-vitro against *Trypanosoma rhodesiense* (the agent of sleeping sickness), against *Trypanosoma cruzi* (the agent of Chagas-disease) and against *Leishmania donovani* (the agent of leishmaniasis). Tests were conducted at concentrations which don't induce basal cytotoxicity on murine muscle cells or macrophages. The action observed in this screening is specific against *Leishmania donovani*.

| | T.b. rhodesiense | | T. cruzi | L. donovani | Cytotoxicity | | Test score* |
|---|---|---|---|---|---|---|---|
| | | | | | L-6 | Macroph | r,d,c, |
| TDR-Code | MIC | IC$_{50}$ | MIC | IC$_{50}$ | MIC | MIC | t,-, |
| Standards | 0.011 | 0.0004 | 3.7 | 30 | >100 | >90 | |
| EP10 | 100 | — | 100 | <30 | 100 | 90 | d |
| EP17 | 100 | — | 100 | 20 | >100 | 90 | d |
| EP19 | 100 | — | 100 | 20 | >100 | 90 | d |
| 4 N | 33 | 17 | 100 | 20 | >100 | >90 | d |
| 7N | 11 | 6,9 | 33 | 8 | 100 | 90 | d |
| T1 | >100 | 18,0 | 100 | <30 | 100 | 90 | d |
| T5 | 100 | 17 | 100 | 6 | 100 | 90 | d |
| T6 | 100 | 17 | 100 | <30 | 100 | 90 | d |
| T7 | 100 | 16 | 100 | <30 | 100 | 90 | d |
| T9 | 100 | 16 | 100 | <30 | 100 | 90 | d |
| T10 | 100 | 16 | 100 | <30 | 100 | 90 | d |
| T11 | 100 | 18 | 100 | <30 | 100 | 90 | d |
| T12 | 100 | 20 | | <30 | | 90 | d |

Legend:

| | | |
|---|---|---|
| EP 10 | 1%-concentrate | β-SITOSTERYL-BEHENATE |
| EP 17 | 1%-concentrate | VITAMIN D$_3$-UNDECENOATE |
| EP 19 | 1%-concentrate | VITAMIN D$_3$-OLEATE |
| 4N | 1%-concentrate | QUERCETIN-OCTALAUROYL-GLUCOSIDE |
| 7N | 1%-concentrate | Z-Gly-Phe-VITAMIN D$_3$-ESTER |
| T1 | 1%-concentrate | COEMULGATOR + TENSIDE |
| T5 | 1%-concentrate | 14-OH-10-DEACETYLBACCATIN-III |
| T6 | 1%-concentrate | 3,28-LAUROYL-BACCATIN-III |
| T7 | 1%-concentrate | QUERCETIN-PENTALAURATE |
| T9 | 1%-concentrate | DECALAUROYL-RUTINOSIDE |
| T10 | 1%-concentrate | β-SITOSTERYL-PALMITATE |
| T11 | 1%-concentrate | β-SITOSTERYL-ARACHIDATE |
| T12 | 1%-concentrate | ERGOSTERYL-LAURATE |

What is claimed is:

1. A spontaneously dispersible concentrate, which when diluted with water, 5% glucose solution or physiological sodium salt solution, produces a thermodynamically stable ultramicroemulsion, having micelles with a hydrodynamic radius of 2.2 to 3.0 nm, comprising:

0.5 to 5% by weight of at least one ester selected from one of formulae (I) or (II):

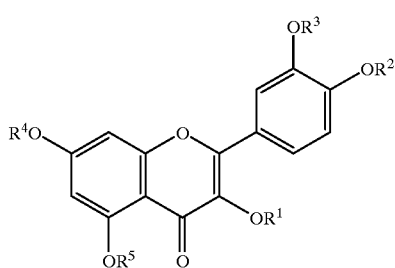

(I)

wherein
(a) $R^1$, $R^3$, $R^4$, and $R^5$ each independently represents a $C_{6-22}$ alkyl, a $C_{6-22}$ alkenyl or a $C_{6-22}$ alkapolyene and $R^2$ is glucose:(1,2);
(b) $R^2$, $R^3$, $R^4$, and $R^5$ each independently represents a $C_{6-22}$ alkyl, a $C_{6-22}$ alkenyl or a $C_{6-22}$ alkapolyene and $R^1$ is glucose:(1,3);
(c) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rhamnose:(1,4); or
(d) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rutinose:(1,5);

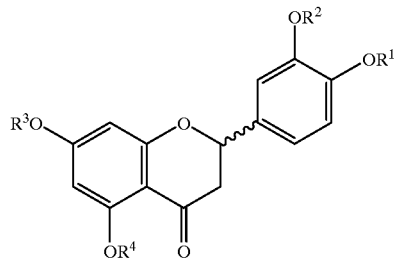

(II)

wherein
(a) $R^1$, $R^2$, and $R^4$ each independently represents a $C_{6-22}$ alkyl, a $C_{6-22}$ alkenyl or a $C_{6-22}$ alkapolyene and $R^3$ is rhamnose:(11,7); or
(b) $R^2$ and $R^4$ each independently represents a $C_{6-22}$ alkyl, a $C_{6-22}$ alkenyl or a $C_{6-22}$ alkapolyene, $R^1$ is methyl, and $R^3$ is rutinose:(11,8);

1 to 25% by weight of a pharmaceutically acceptable hydrotropic agent or coemulgator, 0 to 5% by weight of a buffer, 3-[(3-cholamidopropyl)-dimethylammonio]propanesulfonate, dimethylsulfoxide, or a combination thereof, 5 to 90% by weight of a pharmaceutically acceptable surfactant or mixture of surfactants, 0 to 10% by weight of a vitamin or provitamin, 0 to 10% by weight of a penetration enhancer, radical scavenger, or stabilizer, and optionally one or more pharmaceutically acceptable excipients or diluents.

2. A pharmaceutical composition comprising an aqueous ultramicroemulsion of the spontaneously dispersible concentrate as claimed in claim 1 together with distiled water, 5% glucose solution, or physiological sodium salt solution in a proportion of 1:20 to 1:1,000,000.

3. A spontaneously dispersible concentrate as claimed in claim 1, wherein the at least one ester is octalauroylspiraeoside or rutin-decalaurate.

4. A spontaneously dispersible concentrate, which when diluted with water, 5% glucose solution or physiological sodium salt solution, produces a thermodynamically stable ultramicroemulsion, having micelles with a hydrodynamic radius of 2.2 to 3.0 nm, comprising:

0.5 to 5% by weight of at least one ester selected from one of formulae (I) or (II):

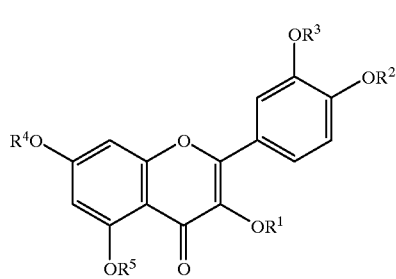

(I)

wherein
(a) $R^1$, $R^3$, $R^4$, and $R^5$ each independently represents a $C_{6-22}$ alkyl, a $C_{6-22}$ alkenyl or a $C_{6-22}$ alkapolyene and $R^2$ is glucose:(1,2);
(b) $R^2$, $R^3$, $R^4$, and $R^5$ each independently represents a $C_{6-22}$ alkyl, a $C_{6-22}$ alkenyl or a $C_{6-22}$ alkapolyene and $R^1$ is glucose:(1,3);
(c) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rhamnose:(1,4); or
(d) $R^2$, $R^3$, $R^4$, and $R^5$ each independently represents a $C_{6-22}$ alkyl, a $C_{6-22}$ alkenyl or a $C_{6-22}$ alkapolyene and $R^1$ is rutinose:(1,5);

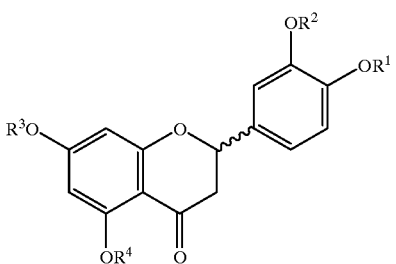

(II)

wherein
(a) $R^1$, $R^2$, and $R^4$ each independently represents a $C_{6-22}$ alkyl, a $C_{6-22}$ alkenyl or a $C_{6-22}$ alkapolyene and $R^3$ is rhamnose:(11,7); or
(b) $R^2$ and $R^4$ each independently represents a $C_{6-22}$ alkyl, a $C_{6-22}$ alkenyl or a $C_{6-22}$ alkapolyene, $R^1$ is methyl, and $R^3$ is rutinose:(11,8);

1 to 25% by weight of isopropylmyristate, isopropylpalmitate, neutral oil, and/or at least one biotenside terpinyl ester of formula (VII)

$$R^6\text{—COO—}R^7 \qquad (VII)$$

wherein R6 is a C6-31 alkyl, a C9-31 alkenyl, or a C9-31 alkapolyene group and R7 is citronellyl, farnesyl, geranyl, isophytyl, or phytyl, 0 to 2% by weight of dimethylsulfoxide 5 to 45% by weight of a phosphoric acid ester tenside and/or of a polyoxyethylene-(20)-sorbitan ester compound, 5 to 90% by weight of waterfree tert-octylphenylpolyoxyethylene ether tenside having 9 to 10 oxyethylene groups, and optionally up to 10% by weight of a vitamin or provitamin.

5. A compound of formula (III) or (IV):

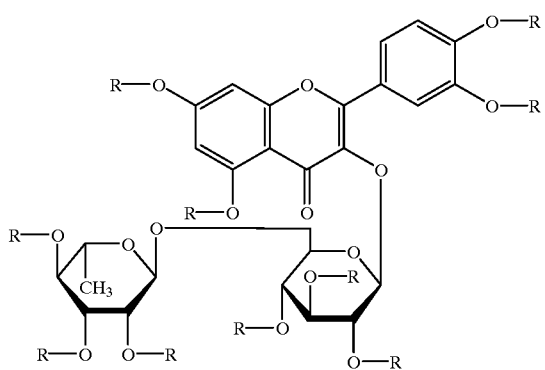

(IV)

wherein each R independently represents a $C_{6-22}$ alkyl, a $C_{6-22}$ alkenyl or a $C_{6-22}$ alkapolyene carboxyl group.

6. A process for preparing a compound of claim 5 comprising reacting the fatty tail principle of formula (III) or (IV) under a protective gas in waterfree pyridine and 1,2-dichloroethane with a chloride of a saturated or unsaturated $C_{6-22}$ alkyl, a $C_{6-22}$ alkenyl or a $C_{6-22}$ alkapolyene carbonic acid with addition of a catalytic amount of 4-dimethylaminopyridine.

7. A pharmaceutical composition comprising a spontaneously dispersible concentrate as claimed in claim 1 in the form of a micropellets, granules, coated pills, suppositories, ampoules, or capsules.

8. A pharmaceutical composition comprising 11 parts by weight of a core material for granulation or pelleting, 25 parts by weight of the concentrate of claim 1, and 31 parts by weight of a slow-release coating of hydroxypropylmethylcellulose-acetate-succinate, in the form of micropellets, granules coated pills, suppositories, amploules, or capsules.

9. A pharmaceutical composition comprising 64 parts by weight of a core material for granulation or pelleting and 36 by weight of the concentrate of claim 1 filled into capsules made of hydroxypropylmethylcellulose-acetate-succinate, in the form of micropellets, granules, coated pills, suppositories, amploules, or capsules.

* * * * *